United States Patent
Rangisetty et al.

(10) Patent No.: US 10,106,489 B2
(45) Date of Patent: Oct. 23, 2018

(54) PROCESS FOR THE PURIFICATION OF POLYAMINOCARBOXYLATES

(71) Applicant: Biophore India Pharmaceuticals Pvt. Ltd., Hyderabad, Andhra Pradesh (IN)

(72) Inventors: Jagadeesh Babu Rangisetty, Hyderabad (IN); Manik Reddy Pullaguria, Hyderabad (IN); Rajesh Bhudeti, Hyderabad (IN)

(73) Assignee: Biophore India Pharmaceuticals Pvt. Ltd., Hyderabad, Andhra Pradesh (IN)

(*) Notice: Subject to any disclaimer, the term of this patent is extended or adjusted under 35 U.S.C. 154(b) by 0 days.

(21) Appl. No.: 14/360,059

(22) PCT Filed: Nov. 26, 2012

(86) PCT No.: PCT/IN2012/000768
§ 371 (c)(1),
(2) Date: May 22, 2014

(87) PCT Pub. No.: WO2013/076743
PCT Pub. Date: May 30, 2013

(65) Prior Publication Data
US 2014/0323719 A1    Oct. 30, 2014

(30) Foreign Application Priority Data
Nov. 25, 2011 (IN) ............... 4068/CHE/2011

(51) Int. Cl.
| | | |
|---|---|---|
| *C07C 227/40* | (2006.01) |
| *C07C 227/42* | (2006.01) |
| *C07C 229/16* | (2006.01) |
| *C07C 229/26* | (2006.01) |
| *C07D 257/02* | (2006.01) |

(52) U.S. Cl.
CPC .......... *C07C 227/42* (2013.01); *C07C 227/40* (2013.01); *C07C 229/26* (2013.01); *C07D 257/02* (2013.01)

(58) Field of Classification Search
CPC ... C07C 227/40; C07C 227/42; C07C 229/26; C07C 229/16; C07D 257/02
See application file for complete search history.

(56) References Cited

U.S. PATENT DOCUMENTS

| | | | |
|---|---|---|---|
| 3,043,867 A | 7/1962 | Anderson | |
| 5,491,259 A | 2/1996 | Grierson et al. | |
| 5,595,714 A * | 1/1997 | Ripa | C01F 17/0006 423/21.1 |
| 5,922,862 A * | 7/1999 | Murru et al. | 540/474 |

FOREIGN PATENT DOCUMENTS

WO    2014/068589 A2    5/2014

OTHER PUBLICATIONS

Platztech et al., Inorg. Chem., 1997, 36, 6086-6093.*
Platzek, J. et al: "Synthesis and Structure of a New Macrocyclic Polyhydroxylated Gadolinium Chelate Used as a Contrast Agent for Magnetic Reasonance Imaging", Inorganic Chemistry, (1997), vol. 36, No. 26, Abstract only, 1 pg.

* cited by examiner

*Primary Examiner* — Sun Jae Yoo
(74) *Attorney, Agent, or Firm* — Wood Herron & Evans LLP

(57) ABSTRACT

The present invention relates to an improved process for the purification of polyaminocarboxylates such as DOTA, DTPA, DO3A-butrol, BOPTA.

6 Claims, No Drawings

PROCESS FOR THE PURIFICATION OF POLYAMINOCARBOXYLATES

BACKGROUND

The invention relates to the purification of polyaminocarboxylate chelating agents which can be used as MRI contrast agents. Polyaminocarboxylates are part of several drugs which include gadoteric acid, gadobutrol, gadobenic acid, gadopentetate, gadoversetamide, gadodiamide. The key ingredient to all the gadolinium based drugs is the chelate to which the gadolinium binds. Having a highly pure chelate free of any salts and metals is the basis for the preparation of the pure gadolinium based MRI agents.

Some of the chelates include 1,4,7,10-tetraazocyclododecane-, 1,4,7,10-tetraacetic acid (DOTA) for gadoteric acid, Pentetic acid (DTPA) for gadopentetate, BOPTA for gadobenic acid, 10-(1-hydroxymethyl-2,3-dihydroxypropyl)-1,4,7-tris(carboxymethyl)-1,4,7,10 tetraazocyclododecane (DO3A-butrol) for gadobutrol.

STATE OF THE ART

Some of the chelates reported in the literature involve complex and expensive purification methods which involve resins of various kinds.

U.S. Pat. No. 5,922,862 describes a procedure for the purification of DOTA and other cyclen substituted derivatives. It describes a procedure for the removal of inorganic salts by elution of the crude product dissolved in water over PVP resin.

Inorg. Chem. 1980, 19, 1319 describes a procedure for the purification of DOTA using Dowex 50W-X4 resin.

Inorg. Chem. 1997, 36, 6086 describes a procedure for the purification of DO3A-butrol with IR120H+ resin to remove salts.

Likewise several other resins are reported for the purification of the chelates to remove inorganic salts. The resin methods involved are expensive and some of the chelates bind to the resins, which then require washing with ammonia solution or formic acid solutions. Removal of ammonium ions becomes particularly difficult as the ligand forms ammonium salts.

The manufacturing of the chelates becomes difficult when large ion-exchange columns are required at commercial scale manufacturing. Since most of the chelates have high water solubility the distillation of water becomes time consuming and also leads to potential degradation products.

SUMMARY OF THE INVENTION

One of the objects of the invention was to provide a process for the preparation of the chelates in the pure form without the presence of impurities such as inorganic salts and other ions such as chloride, bromide, sulphate or the like.

Yet another object of the invention was to develop a process with low cycle time, which is commercially viable, inexpensive and which utilizes none or minimal amount of resin.

DETAILED DESCRIPTION OF THE INVENTION

The purification procedure of chelates without ion-exchange column purifications are particularly advantageous as they are less time consuming and are rather inexpensive.

It has now surprisingly been found that polyaminocarboxylate compounds when isolated under highly acidic conditions preferably below 0.75 are isolated as their acid salts and upon purification of these salts by recrystallization from water or water solvent mixtures result in polyaminocarboxylate with a content of any inorganic salts or ions such as sodium, potassium or the like below 200 ppm. The acid employed for the salt formation can be hydrochloric acid, hydrobromic acid, sulfuric acid and the like. The acid is preferably hydrochloric acid and the salt isolated is as hydrochloride salt.

The water solvent mixtures employed are water/acetone, water/ethanol, water/methanol or the like to obtain a product free of undesired chloride or bromide ions, which have very stringent specifications.

The salt thus obtained is dissolved in water and is then adjusted to the desired pH either with an aqueous basic solution or alternatively a resin. It is noteworthy to mention here that the amount of resin employed is minimal and is used to adjust the pH of the solution about 1.5-3.0, thereby eliminating the chance for any additional inorganic salt formation. As the resin employed is in minimal amounts the process does not suffer from the drawbacks of the prior art. The pH is preferably adjusted with a basic anionic resin.

The resins that are employed in the current process are resin in the hydroxide form such as Amberlyst A26 OH resin and the like. The bases that can be employed for the pH adjustment are potassium hydroxide, sodium hydroxide, ammonium hydroxide, triethyl amine or the like.

An example of the process schematics is shown below for DOTA. The example described for DOTA is not limiting and a similar purification process can be applied to any polyaminocarboxylate.

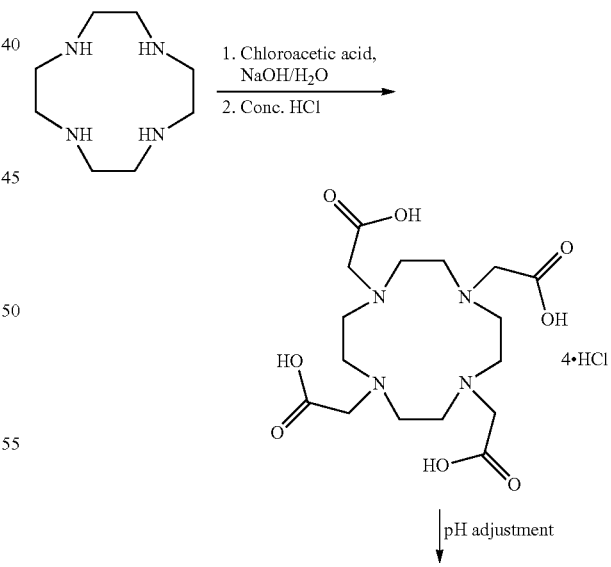

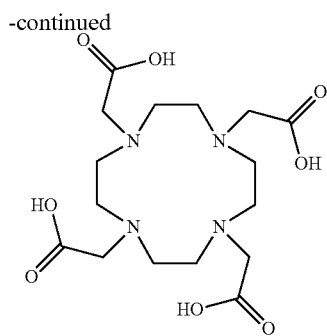

The following examples describe the process in greater detail.

Example 1: Synthesis of DOTA

Charge 100 ml of water and 100 g cyclen HCl to a flask. Cool the reaction mass to 0-10° C. and adjust the pH of the solution to 10-10.5 with sodium hydroxide. Charge chloroacetic acid to the reaction with continuous pH adjustment to 10-10.5 with sodium hydroxide solution. Slowly raise the reaction to 70-75° C. and maintain until the completion of reaction. Cool the reaction mass and adjust the pH of the reaction to below 0.75 with conc. HCl and filter the solid separated which is DOTA hydrochloride. Recrystallize the solid from water and check the content of sulfated ash to be below 0.10%. The solid is then dissolved in 800 ml water and the pH of the solution adjusted to around 2.5 to 3.0 with amberlyst A26 OH resin to obtain a chelate free of hydrochloride salt. The mass is then filtered, and the filtrate obtained is distilled to 200-300 ml water and the solid is precipitated by adding acetone. The solid is filtered and dried to give the title product with desired purity having sulfated ash content below 0.1% and the sodium and chloride content below 200 ppm.

Example 2: Synthesis of BOPTA

To a flask were charged 100 ml of water and 50 g of N-[2-[(2-aminoethyl)amino]ethyl]-O-(phenylmethyl)serine. Cool the reaction mass to 0-10° C. and adjust the pH of the solution to 10.5-11.5 with sodium hydroxide solution. Charge chloroacetic acid to the reaction with continuous pH adjustment to 10.5-11.5 with sodium hydroxide solution. Slowly raise the reaction temperature to 70-75° C. and maintain until the completion of reaction. Cool the reaction mass and adjust the pH of the reaction to below 0.75 with Conc. HCl and charge acetone. Filter the solid separated which is BOPTA hydrochloride salt. Recrystallize the solid from water and check the sulfated ash content to be below 0.10%. The solid is then dissolved in 800 ml water and the pH of the solution adjusted to around 2.0 with amberlyst A26 OH resin. The mass is then filtered and the filtrate is distilled to 200-300 ml water and the solid is precipitated by adding acetone. The solid thus obtained is filtered and dried to give the product with desired purity having sulfated ash below 0.1%.

The invention claimed is:

1. A process for the purification of polyaminocarboxylate chelating agent selected from the group consisting of DOTA, which comprises:
   a) treating an aqueous solution of polyaminocarboxylate with an inorganic acid, wherein the pH of the solution is below 0.75;
   b) recrystallizing the precipitated polyaminocarboxylate acid salt in water to obtain a solid and dissolving it in water to give an aqueous solution of polyaminocarboxylate acid salt;
   c) treating the aqueous solution of polyaminocarboxylate acid salt from step b) with a resin or a basic solution to maintain pH at 1.5 to 3.0; and
   d) isolating pure polyaminocarboxylate chelating agent;
   wherein after the step (a) above, the product obtained is precipitated as polyaminocarboxylate acid salt;
   wherein the precipitated polyaminocarboxylate acid salt as obtained in above step (a) is isolated by filtration before performing the step of recrystallization in step (b); and wherein, resin in step (c) is employed to adjust the pH of the solution.

2. The process of claim 1 wherein the inorganic acid employed is selected from hydrochloric acid, hydrobromic acid, and sulfuric acid.

3. The process of claim 1 wherein the polyaminocarboxylate purified is DOTA and the inorganic acid employed is hydrochloric acid.

4. The process of claim 1 wherein the resin employed is basic anionic resin.

5. The process of claim 1 wherein the polyaminocarboxylate isolated contains sodium, potassium, sulfate, chloride, bromide, and ammonium salt impurities below 200 ppm.

6. The process of claim 1, wherein the precipitated polyaminocarboxylate acid salt as produced and isolated after step (a) is polyaminocarboxylate hydrochloride salt.

* * * * *